(12) United States Patent
Watanabe et al.

(10) Patent No.: US 6,551,582 B2
(45) Date of Patent: Apr. 22, 2003

(54) DEODORANT COMPOSITION

(75) Inventors: Keisuke Watanabe, Ashiya (JP); Michihiko Fujinami, Minoo (JP)

(73) Assignee: Sumitomo Chemical Company, Limited, Osaka (JP)

( * ) Notice: Subject to any disclaimer, the term of this patent is extended or adjusted under 35 U.S.C. 154(b) by 0 days.

(21) Appl. No.: 10/041,741

(22) Filed: Jan. 10, 2002

(65) Prior Publication Data

US 2002/0141962 A1 Oct. 3, 2002

(30) Foreign Application Priority Data

Jan. 23, 2001 (JP) ........................ 2001-014262

(51) Int. Cl.[7] .............. A61L 9/00; A61L 9/01; A61L 9/04; A61L 11/00; A61K 9/00
(52) U.S. Cl. .................. 424/76.1; 424/76.3; 424/76.5; 424/76.6; 424/76.7; 424/76.8; 424/400
(58) Field of Search .................. 424/400, 76.1, 424/76.3, 76.5, 76.6, 76.7, 76.8

(56) References Cited

U.S. PATENT DOCUMENTS 5,714,137 A * 2/1998 Trinh et al.
5,942,478 A 8/1999 Lopes

FOREIGN PATENT DOCUMENTS

DE 24 56 639 6/1976
JP 57-49220 10/1982

OTHER PUBLICATIONS

Patent Abstracts of Japan, vol. 1999, No. 09, Jul. 30, 1999 (corresponding to JP 11–116830).
S. Nakahara et al., "Acidic Compounds in Patchouli Oil", Phytochemical Reports, (1975), pp. 2712–2713.

* cited by examiner

Primary Examiner—Gollamudi S. Kishore
Assistant Examiner—Simon J. Oh
(74) Attorney, Agent, or Firm—Sughrue Mion, PLLC

(57) ABSTRACT

A deodorant composition, which comprises a pyrone compound given by formula:

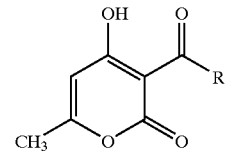

wherein R represents a C3–C10 acyclic hydrocarbyl group, as an active ingredient, is very effective for removing bad smell.

4 Claims, No Drawings

DEODORANT COMPOSITION

FIELD OF INVENTION

The present invention relates to a deodorant composition. In detail, it relates to a composition for removing smell originated from excreta of humans, cattle and pets, and so on.

BACKGROUND ART

Recently, people sensitive to odor are increasing by much sanitary consciousness. Now, it is needed to remove or restrict smell originated from garbage, toilets and so on. There exist many kinds of substances due to bad smell, and their examples include mercaptans, ammonia and amines originated from excreta of toilets and pets; hydrogen sulfide and amines originated from rotten foods; lower fatty acids such as acetic acid, butyric acid, propionic acid, isovaleric acid and so on originated from sweat and body odor. Many deodorant compositions are developed corresponding to substances and places causing odor.

It is known that a composition containing dehydroacetic acid of formula:

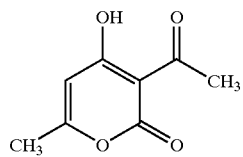

and glyoxal has a deodorant effect against smell originated from excreta in JP-sho-50-126825A. However, it is not necessarily sufficient a deodorant effect of the composition containing dehydroacetic acid as a deodorant active ingredient.

SUMMARY OF THE INVENTION

The present invention gives a deodorant composition comprising a pyrone compound given by formula (I):

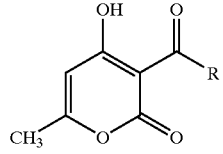

wherein R represents a C3–C10 acyclic hydrocarbyl group, as an active ingredient and a carrier, which has an excellent deodorant effect against ammonia and amines.

DISCLOSURE OF THE INVENTION

Namely, the present invention provides a deodorant composition comprising the pyrone compound given by the formula (I) as an active ingredient.

The present deodorant composition, which can be prepared by mixing the pyrone compound with a suitable carrier to be formulated to liquid, solid or gel composition, is utilized by applying to the places where smell generates or drifts. The content of the pyrone compound in the present deodorant composition is generally 0.01 to 60% by weight, preferably 1 to 30% by weight.

Examples of the carriers mixed with the pyrone compound include liquid carriers, solid carriers and gel carriers.

Examples of the liquid carrier for preparing liquid formulations include water; C1–C6 monovalent alcohols such as methanol, ethanol, propanol, isopropyl alcohol and amyl alcohol; C2–C6 polyvalent alcohols such as glycerin, butyldiglycol (diethylene glycol monobutyl ether), ethylene glycol and propylene glycol; polyethylene glycol; and glycol alkyl ethers such as ethylene glycol monobutyl ether, ethylene glycol monoethyl ether, diethylene glycol monobutyl ether, diethylene glycol monoethyl ether, propylene glycol monobutyl ether and dipropylene glycol monobutyl ether.

The liquid formulations can optionally contain a formulation auxiliary such as surfactant, preservative and propellant. Typical examples are surfactants such as soaps, polyoxyethylene fatty acid alcohol ethers (e.g. polyoxyethylene oleyl ether), polyoxyethylenealkyl aryl ethers (e.g. polyoxyethylenenonyl phenyl ether), polyoxyethylene fatty acid esters, fatty acid glycerides, sorbitan fatty acid esters, sulfate esters of higher alcohols and alkylarylsulfonate salts (e.g. sodium dodecylbenzenesulfonate); and preservatives such as methyl 4-hydroxybenzoate, ethyl 4-hydroxybenzoate, propyl 4-hydroxybenzoate and butyl 4-hydroxybenzoate.

The liquid formulation is usually utilized by spraying to the place where bad smell generates. For spraying, the liquid formulation may be charged into a container equipped with spray mechanism or a pressure container with a propellant (e.g. liquefied petroleum gas, dimethyl ether, nitrogen gas, liquefied carbon dioxide gas, flon 11, flon 12).

The liquid formulation can be also utilized by penetrating into paper, cloth or the like by capillary action and exposing a wide area to odor drifting in an air. Examples of the paper and cloth used for the method include filter paper and non-woven cloth.

Examples of the solid carrier for preparing the solid formulations include mineral solids such as silicate salts, kaolin, activated carbon, zeolite, bentonite, diatomaceous earth, talc, silica gel and calcium carbonate; plant solids such as wood chip, paper, peat moss and coffee bean shell; and synthetic resins such as polyvinyl chloride. The shape of the solid carrier can be granules or powders.

The solid formulations can be prepared by spraying, or by penetrating the above-described liquid formulation to the solid carrier and then optionally vaporizing the liquid carrier.

The solid formulation is usually utilized by distributing or spreading on the place where bad smell generates, or surroundings.

The gel carrier for preparing the gel formulations can be prepared from gelatinizers such as carrageenan, agar, locust bean gum, polyvinyl alcohol, gum arabic, gellan gum, gelatin, carboxymethylcellulose, sodium alginate and sodium stearate.

The gel formulation may contain a surfactant, if needed. Typical surfactants are soaps, polyoxyethylene fatty acid alcohol ethers (e.g. polyoxyethylene oleyl ether), polyoxyethylenealkyl aryl ethers (e.g. polyoxyethylenenonyl phenyl ether), polyoxyethylene fatty acid esters, fatty acid glycerides, sorbitan fatty acid esters, sulfate esters of higher alcohols and alkylarylsulfonate salts (e.g. sodium dodecylbenzenesulfonate).

The gel formulation is utilized by setting on the place where bad smell generates or surroundings or by exposing to odor drifting in an air.

The present composition can contain an additive such as antioxidant, pigment, coloring agent, stabilizer and UV absorbent. Further, known deodorant, perfume, antimicrobial, fungicide, insecticide, acaricide or pest repellent may be mixed or used together.

The present composition is excellent at deodorizing amines originated from excreta of humans, cattle and pets, and rotten foods in particular. Therefore, it is effective to use the present composition at the place where bad smell generates, such as privy (latrine), toilet for pets, cattle shed, garbage at kitchen and dumping ground.

In the pyrone compound given by the formula (I), that is the active ingredient of the present composition, C3–C10 acyclic hydrocarbyl group for R is exemplified by straight-chain or branched C3–C10 alkyl, straight-chain or branched C3–C10 alkenyl and straight-chain or branched C3–C10 alkynyl.

Examples of the pyrone compound include the compounds listed in Table 1, but the compound is not limited to them.

TABLE 1

| Compound Nos. | R |
|---|---|
| 1 | $CH_2CH_2CH_3$ |
| 2 | $CH_2CH_2CH_2CH_3$ |
| 3 | $CH_2CH_2CH(CH_3)_2$ |
| 4 | $CH_2CH_2CH_2CH_2CH_3$ |
| 5 | $CH(CH_3)CH_2CH_2CH_3$ |
| 6 | $CH_2CH_2CH_2CH_2CH_2CH_3$ |
| 7 | $CH_2CH_2CH_2CH_2CH_2CH_2CH_3$ |
| 8 | $CH_2CH_2C\equiv CH$ |

The pyrone compound given by the formula (I) may be utilized solely or as a mixture thereof at any rate in the present deodorant composition.

The pyrone compound can be produced from 4-hydroxy-6-methyl-2-pyrone and so on by the method described in JP-sho51-19126A or WO97/35565.

EXAMPLES

The present invention will be illustrated in more details by production examples and test examples, although the present invention is not limited in any sense to these examples.

At first, the production examples of the present composition are given. Parts represent parts by weight and the pyrone compounds given by the formula (I) are shown by Compound numbers in Table 1.

Production Example 1

To a mixture of 80 parts of ethanol and 15 parts of water, 5 parts of each of Compounds 1–8 were added and stirred, and filtered off when insoluble substance is carried down, to give a liquid formulation for spraying.

Production Example 2

To a mixture of 80 parts of isopropyl alcohol and 15 parts of water, 5 parts of each of Compounds 1–8 were added and stirred, and filtered off when insoluble substance is carried down, to give a liquid formulation for spraying.

Production Example 3

To a mixture of 80 parts of glycerin and 15 parts of water, 5 parts of each of Compounds 1–8 were added and stirred, and filtered off when insoluble substance is carried down, to give a liquid formulation for spraying.

Production Example 4

To a mixture of 93 parts of ethanol and 2 parts of water, 5 parts of each of Compounds 1–8 were added and stirred, and filtered off when insoluble substance is carried down, to give a liquid formulation for spraying.

Production Example 5

Each of Compounds 1–8 was dissolved in ethanol to give a 10mg/ml liquid formulation.

Production Example 6

To 100 g of natural sand, 10 ml of acetone solution of Compound 3 (1% by weight) were sprayed, mixed well and air-dried to give a solid formulation.

Production Example 7

To 100 g of bentonite, 10 ml of ethanol solution of Compound 3 (10% by weight) were sprayed, mixed well and air-dried to give a solid formulation.

Production Example 8

Ten parts of each of Compounds 1–8 were dissolved in ethanol to make the total 35 parts, and placed in an aerosol vessel. The vessel was equipped with a valve, and then 65 parts of propellant (mixture of flon 11 and flon 12 at 1:1) were charged through the valve under pressure to give an aerosol.

Next, a preparing example of the pyrone compound given by general formula chemical 2 is shown below.

Preparation Example 1

Ten grams (10.0 g, 79.3 mmol) of 4-hydroxy-6-methyl-2-pyrone were suspended in 100 ml of toluene at room temperature. To the suspension, 1.22 g (10.0 mmol) of N,N-dimethylaminopyridine, 10.0 g (86.1 mmol) of isocaproic acid and 18.5 g (89.7 mmol) of dicyclohexylcarbodiimide were added subsequently. The mixed solution was stirred for one hour at room temperature, and then heated to 70° C. and stirred for 20 hours under heating. After the mixed solution was allowed to stand at room temperature, the precipitated insoluble dicyclohexylurea was filtered off, and washed with 1N hydrochloric acid once and 10% brine twice. The organic layer was dried over magnesium sulfate and evaporated under reduced pressure to give a crude oily product.

The crude oily product was subjected to silica gel column chromatography (eluent: hexane/ethyl acetate=6/1) to give 7.11 g of Compound 3 (yield 40%).

$^1$H-NMR (CDCl$_3$/TMS): 0.94 (6H, d), 1.54 (2H, q), 1.63 (1H, m), 2.27 (3H, s), 3.08 (2H, t), 5.93 (1H, s), 17.88 (1H, s) mp 42° C.

The physical properties of the pyrone compound given by the formula (I), prepared according to the method described in Preparation example 1, are given below.

| | |
|---|---|
| Compound 1 | mp 59° C. |
| Compound 2 | mp 76° C. |
| Compound 4 | $^1$H-NMR (CDCl$_3$/TMS):0.91 (3H, t), 1.36 (4H, m), 1.67 (2H, m), 2.27 (3H, s), 3.07 (2H, t), 5.93 (1H, s), 16.88 (1H, s) |
| Compound 5 | mp 66° C. |
| Compound 6 | mp 74° C. |
| Compound 7 | mp 66° C. |
| Compound 8 | mp 193° C. |

Next, the deodorant effect of the present composition is shown in the following test examples.

Test Example 1

Into a glass Erlenmeyer flask (1L-volume), 1 mL of 1.8% aqueous solution of ammonia was placed at room temperature (about 20° C.). After the flask was sealed with a rubber stopper and shaken to be filled with ammonia gas, the concentration of ammonia was measured with a gas detector tube (No. 3HM, Gastec Corporation).

Next, 1 mL of each formulation obtained in Production example 1 was sprayed into the flask. The concentration of ammonia was measured with a gas detector tube (No. 3HM, Gastec Corporation) after 30 minutes. A control solution (1 mL) of a mixed solvent without the present deodorant compound was added into an Erlenmeyer flask (1 L-volume) containing ammonia gas, and then the conversation of ammonia was measured with the same method after 30 minutes.

Dehydroacetic acid was formulated in the same manner as Production example 1, and then comparative test was carried out by the same method.

The formulations obtained in Production example 2 and 3 were provided to the same test.

The results are given in Table 2. Deodorant rates were calculated by formula 1.

Deodorant rate (%) =

$$\left(1 - \frac{\text{concentration of ammonia in tested area}}{\text{concentration of ammonia in control area}}\right) \times 100$$

TABLE 2

| | Deodorant rate (%) | | |
|---|---|---|---|
| Compound Nos. | Production example 1 | Production example 2 | Production example 3 |
| 1 | 80 | 70 | 60 |
| 2 | 70 | 60 | 60 |
| 3 | 100 | 95 | 90 |
| 4 | 80 | 80 | 80 |
| 5 | 100 | 90 | 90 |
| Dehydroacetic acid | 20 | 25 | 25 |

Test Example 2

Into a glass Erlenmeyer flask (2 L-volume), 5 mL of 0.03% aqueous trimethylamine solution were placed at room temperature (about 20° C.). After the flask was sealed with a rubber stopper and shaken to be filled with trimethylamine gas, concentration of trimethylamine was measured with a gas detector tube (No. 180, Gastec Corporation).

Next, 1 mL of each formulation obtained in Production example 5 was sprayed into the flash. The concentration of trimethylamine was measured with a gas detector tube (No. 180, Gastec Corporation) after 30 minutes. A control solution (1 mL) of ethanol was added into the flask, and then the concentration of trimethylamine was measured with the same method after 30 minutes.

The results are given in Table 3. Deodorant rates were calculated by formula 2.

Deodorant rate (%) =

$$\left(1 - \frac{\text{concentration of trimethylamine in tested area}}{\text{concentration of trimethylamine in control area}}\right) \times 100$$

TABLE 3

| Compound Nos. | Deodorant rate (%) |
|---|---|
| 1 | 100 |
| 2 | 100 |
| 3 | 100 |
| 4 | 95 |
| 6 | 95 |
| 7 | 95 |

Test Example 3

One hundred grams (100 g) of the formulation obtained in Production example 6 were placed on a circular filter paper (20 cm in diameter) in a desiccator (30 cm in meter). Ten milliliters (10 mL) of 1.8% aqueous ammonia solution were sprayed thereto, and the solid formulation was stirred. The desiccator was sealed for 2 minutes and the concentration of ammonia in the desiccator was measured with a gas detector tube (No. 3La, Gastec Corporation) after 5 minutes and 60 minutes respectively.

For control test, 100 g of sand were placed on a circular filter paper (20 cm in desiccator (30 cm in diameter). Ten milliliters (10 mL) of 18% aqueous ammonia solution were sprayed thereto, and the sand was stirred. The desiccator was sealed for 2 minutes and the concentration of ammonia was measured by the same method after 5 minutes and 60 minutes respectively.

The results are given in Table 4.

TABLE 4

| Compound No. | after 5 minutes | after 60 minutes |
|---|---|---|
| 3 | 3 ppm | No detected |
| Control | 80 ppm | 50 ppm |

Test Example 4

In a 5 L-volume desiccator, 100 g of toilet sand for pets (bentonite) impregnated with cat urine were placed. The concentration of ammonia in the desiccator was measured with a gas detector tube (No. 3HM, Gastec Corporation) at room temperature (about 20° C.) to afford 300 ppm. To the toilet sand, 10 mL of the formulation of Compound 4 obtained in Production example 3 were sprayed. The concentration of ammonia in the desiccator was measured with a gas detector tube (No. 3La, Gastec Corporation) after 60 minutes. As a result, the concentration was decreased to 20 ppm.

The present composition has an excellent deodorant effect against odor originated from ammonia and amines in environment.

We claim:

1. A deodorant composition which comprises 1% to 60% of a pyrone compound given by formula:

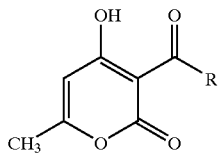

wherein R represents a C3–C10 acyclic hydrocarbyl group, as an active ingredient; and a carrier comprising water, a C1 to C6 monovalent alcohol, a C2 to C6 polyvalent alcohol, polyethylene glycol, or glycol alkyl ethers.

2. A deodorant composition according to claim 1, wherein R is propyl, butyl, 3-methylbutyl, pentyl, 1-methylbutyl, hexyl, heptyl or 3-butynyl.

3. A method for removing smell which comprises applying an effective amount of a pyrone compound given by formula:

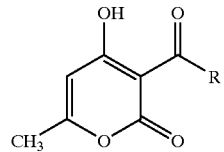

wherein R represents a C3–C10 acyclic hydrocarbyl group, to a place generating or drifting smell.

4. A method for removing smell according to claim 3, wherein R is propyl, butyl, 3-methylbutyl, pentyl, 1-methylbutyl, hexyl, heptyl or 3-butynyl.

* * * * *